(12) United States Patent
Blalock

(10) Patent No.: US 11,744,663 B2
(45) Date of Patent: Sep. 5, 2023

(54) PUNCTURE-RESISTANT RADIOLUCENT OPERATING SURFACE

(71) Applicant: Ryan Eric Blalock, Dallas, TX (US)

(72) Inventor: Ryan Eric Blalock, Dallas, TX (US)

(*) Notice: Subject to any disclaimer, the term of this patent is extended or adjusted under 35 U.S.C. 154(b) by 281 days.

(21) Appl. No.: 17/330,347

(22) Filed: May 25, 2021

(65) Prior Publication Data
US 2022/0378539 A1  Dec. 1, 2022

(51) Int. Cl.
| | | |
|---|---|---|
| A61B 5/00 | (2006.01) | |
| A61B 46/10 | (2016.01) | |
| A61B 90/00 | (2016.01) | |
| A61B 17/00 | (2006.01) | |

(52) U.S. Cl.
CPC .............. *A61B 46/10* (2016.02); *A61B 90/36* (2016.02); *A61B 2017/0092* (2013.01); *A61B 2090/3764* (2016.02)

(58) Field of Classification Search
CPC . A61B 46/10; A61B 90/36; A61B 2090/3764; A61B 2017/0092
See application file for complete search history.

(56) References Cited

U.S. PATENT DOCUMENTS

2013/0167845 A1* 7/2013 Grajek ................. A01K 39/012
128/856

* cited by examiner

*Primary Examiner* — Joel F Brutus
(74) *Attorney, Agent, or Firm* — Kendall Burr

(57) ABSTRACT

A puncture-resistant radiolucent operating surface apparatus includes a flat radiolucent and puncture-resistant surface configured to cover the detector of an intraoperative imaging machine, and downwardly extending sidewall flanges that are connected to said flat surface and that conform to the sides of said detector.

14 Claims, 7 Drawing Sheets

PUNCTURE-RESISTANT RADIOLUCENT OPERATING SURFACE

BACKGROUND OF THE INVENTION

1. Technical Field

The present invention relates to providing a sterile operating environment that facilitates the use of intra-operative imaging (for example, X-ray) equipment.

2. Description of Related Art

Intraoperative imaging, particularly fluoroscopy (X-ray) imaging, is an invaluable tool for many surgical fields. Orthopedic surgery, in particular, relies extensively on intraoperative imaging. To maintain a sterile environment during surgery, the typical practice is to use protective, flexible, sterile, and radiolucent covers, which are typically draped over the intraoperative imaging machines and tied off to ensure that the equipment is covered with a protective but radiolucent sterile barrier. Intraoperative imaging machines used in such orthopedic surgeries often consist of what is commonly referred to as a "C-arm" imaging machine, which has an X-ray source which generates X-rays which then passes through the patient and operating surface and are captured by a detector placed under the operating surface. The covers or drapes that are commonly used in the operating room are typically customized for use with specific types of C-arm machines or other intraoperative imaging equipment.

However, such covers are often susceptible to puncture because during many procedures sharp instruments and implants make contact with those protective covers. Such punctures may often occur at the portion of the sterile cover that is draped over the detector of the intraoperative imaging machine, at or near the operating surface, where sharp instruments and implants are placed in close proximity to the sterile drape. This can result in breeches in the sterile field resulting in contamination and consequently an increased risk of infection for the patient. Further, because the sterile drape is typically placed directly over the unsterile surface of the intraoperative imaging machine, sharp instruments or implants that puncture the sterile drape can also come into contact with and possibly damage the machine as well. Currently, sufficiently puncture-resistant covers do not exist or are not readily available for use with the intraoperative imaging equipment commonly used in most operating rooms.

As such, what is needed is an apparatus that may be utilized in conjunction with existing intraoperative imaging machines and the sterile covers typically draped over such machines, and that will prevent punctures to said covers and maintain the integrity of the operating environment. The needed solution will provide a puncture resistant radiolucent sterile barrier to prevent contact between sharp instruments and implants and the underlying easily penetrated sterile drape covering the detector of the imaging machine. The needed solution will need to be constructed of a puncture resistant radiolucent sterile material, ideally of a design that may be readily manufactured, and would need to be compatible with existing imaging machines, including detectors of varied shapes and sizes. The needed solution will also be sufficiently low profile so as to not interfere with actions being performed during operation procedures. Finally, the needed solution will need to be secured to the detector of the imaging machine in a manner that prevents displacement or instability of the device during operative procedures.

BRIEF SUMMARY OF THE INVENTION

In one embodiment of the invention, a puncture-resistant radiolucent operating surface apparatus is provided, comprising a flat radiolucent and puncture-resistant surface configured to cover the detector of an intraoperative imaging machine, and downwardly extending sidewall flanges that are connected to said flat surface and that conform to the sides of said detector.

Also in one embodiment, the entire apparatus is comprised of puncture-resistant material. Also in one embodiment, the sidewall flanges are positioned so as to leave a gap to accommodate a horizontally extending arm of the imaging device. Also in one embodiment, the shape of the operating surface and position of the sidewall flanges are customized such that the apparatus is conformed to fit snugly onto a detector of a particular model of an intraoperative imaging machine such that it remains stable when placed in position. Also in one embodiment, the inner surfaces of the sidewall flanges contain dowel pins or other fastening devices enabling the apparatus to be snapped in position when placed on the detector. Also in one embodiment, its inner surfaces are covered with an adhesive to secure the apparatus to the detector or to a flexible cover draped over the detector.

Also in one embodiment, a mechanism provides circumferential pressure around said sidewall flanges in order to stably secure the apparatus on the detector. Also in one embodiment, the mechanism for providing circumferential pressure consists of a zip tie, elastic, or other compressive band positioned around the sidewall flanges of the apparatus. Also in one embodiment, the sidewall flanges of the apparatus contains eyelets through which to thread a zip tie, elastic, or other compressive band. Also in one embodiment, the mechanism for providing circumferential pressure is to connect the sidewall flanges to the flat surface at an acute inner angle such that the sidewall flanges apply lateral pressure around the sides of the detector.

In another aspect of the invention, a method of affixing a puncture-resistant radiolucent operating surface to the detector of an intraoperative imaging machine is provided, comprising the steps (a) covering the detector with a flat radiolucent and puncture-resistant surface, and (b) securing the surface to the detector to ensure that the surface remains stable when the apparatus is placed in position on said detector.

In one embodiment of the method, the inner shape and dimensions of the device are conformed such that it fits snugly onto a detector of a particular model of an intraoperative imaging machine such that it remains stable when placed in position. Also in one embodiment, circumferential pressure is applied around the detector through the means of a zip tie, elastic, or other compressive band. Also in one embodiment, dowel pins or other fastening devices are provided on the inner surfaces of the sidewall flanges to enable the apparatus to be snapped in position when placed on the detector. Also in one embodiment, circumferential pressure is applied around the detector by affixing sidewall components to the flat surface at an acute inner angle such that the sidewalls apply lateral pressure around the sides of the detector. Also in one embodiment, the operating surface is affixed onto the detector through the means of an adhesive.

DETAILED DESCRIPTION OF THE INVENTION

Figure 1:
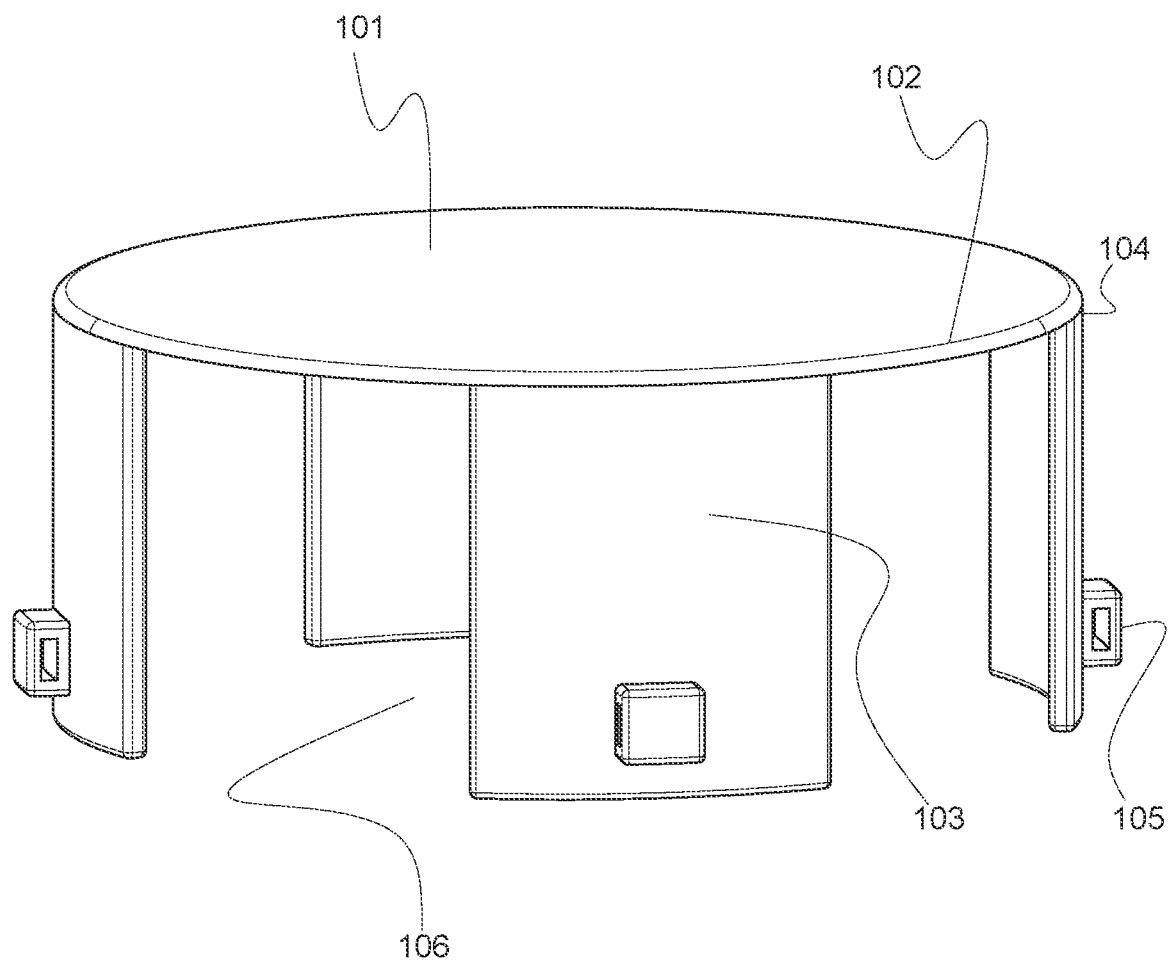
FIG. 1 is a perspective view of a puncture-resistant C-arm detector cover according to an embodiment of the present invention.
Figure 2:
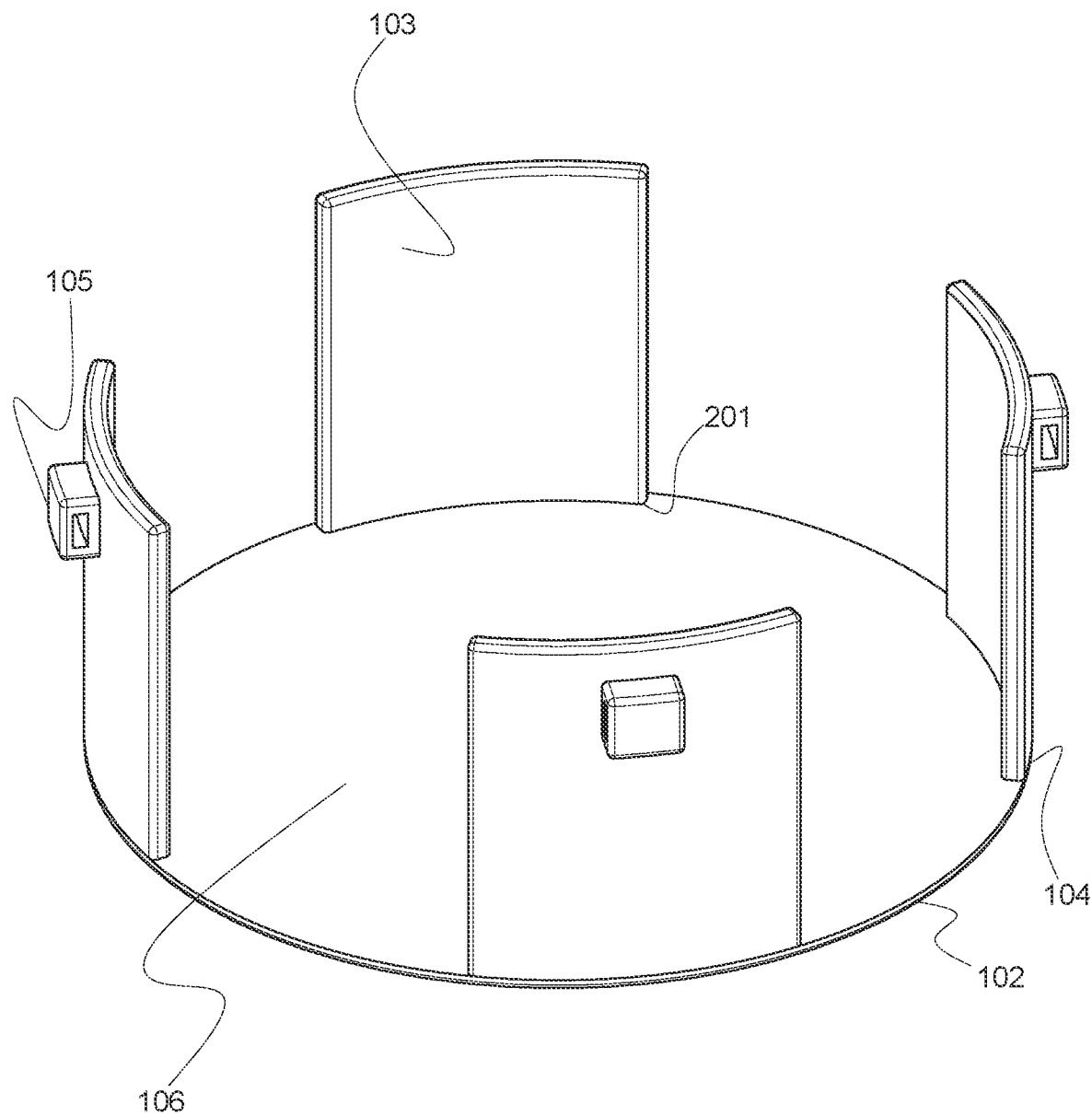
FIG. 2 is another perspective view of the C-arm detector cover in FIG. 1.

Referring in greater detail to the drawings, FIG. 1 and FIG. 2 illustrate a puncture-resistant radiolucent operating surface device, referred to herein as a C-arm detector cover, constructed in accordance with one embodiment of the present invention. In this example, a sterile flat radiolucent surface 101 is provided, composed of rigid radiolucent material so as to provide an operating surface. All edges of the flat surface 101 and other aspects of the C-arm detector cover are rounded, beveled or chamfered 102 so as to avoid introducing sharp edges or corners into the operating environment. The flat surface 101 is also radiolucent so as to permit the passage of X-rays through the C-arm detector cover and reach the detector of the imaging machine. In this example, four sidewall flanges 103 of the same rigid material utilized for the flat surface 101 extend downward and perpendicular to the flat surface 101 to provide stability to the C-arm detector cover as it is placed upon the detector of the intraoperative imaging machine. Other embodiments of the device would feature downwardly projecting sidewall flanges 103 that attach to the flat surface 101 at other angles or in other positions customized to fit the particular shape, design and dimensions of the C-arm detector being covered. In this example, each downwardly projecting sidewall flange 103 adjoins perpendicularly with flat surface 101 such that the joints between those two components are flush 104 and the edge is chamfered 102 as with all other edges and corners of the C-arm detector cover. In this embodiment of the present invention, near the bottom of each sidewall flange 103 there is an eyelet 105 through which a zip tie or similar flexible compressive device may be threaded to tighten the sidewall flanges 103 against the sides of the detector. In other embodiments, such a compressive device may not be necessary where the overall shape of the design conforms sufficiently to the shape of the collector such that it remains in place without any circumferential pressure, where the inner surfaces of the sidewall flanges 103 contain dowel pins or other fastening devices enabling the apparatus to be snapped in position when placed on the detector, or where the inner surfaces of the sidewall flanges 103 and the underside of the flat surface 101 are covered with an adhesive to secure the apparatus to the detector or to a flexible cover draped over the detector. As depicted in FIG. 1, in this example, the overall shape of the C-arm detector cover is cylindrical 106, consisting of a circular flat surface 101 and sidewall flanges 103 that curve with the device's overall cylindrical shape 106. As depicted in FIG. 2, in this example the C-arm detector cover is constructed such that the inner edge 201 of each downwardly projecting sidewall flange 103 will fit snugly around the sides of a C-arm detector of an imaging device with a corresponding cylindrical 106 size and shape.

Figure 3:
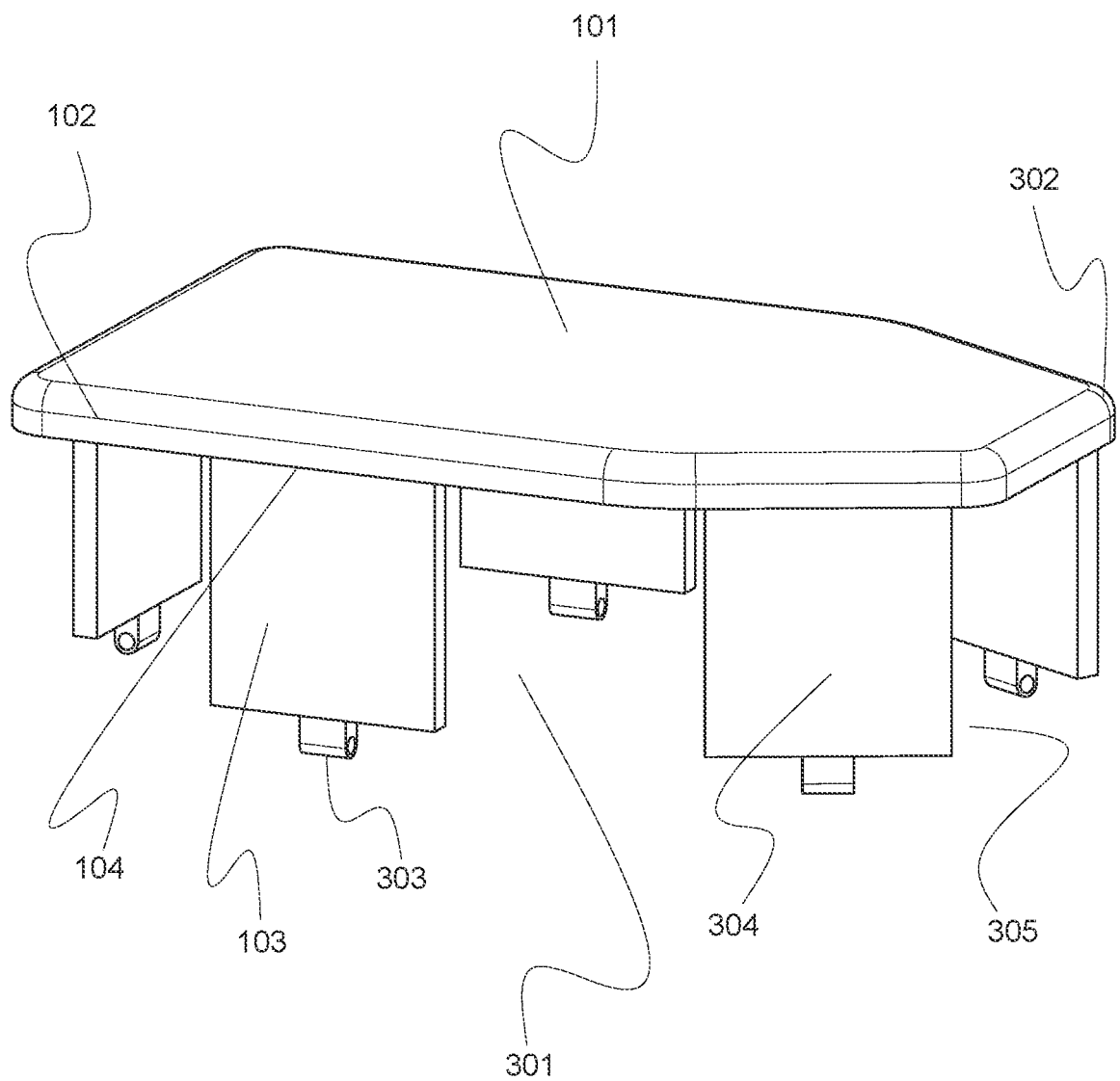
FIG. 3 is a perspective view of a C-arm detector cover according to a further embodiment of the present invention.

FIG. 3 illustrates another example of a C-arm detector cover that, according to another embodiment of the present invention, is designed to fit snugly over a C-arm detector of oblong or rectangular shape 301. In this example, the flat surface 101 has an oblong or rectangular shape 301 customized to fit the shape of the C-arm detector over which it is placed, with corners 302 of the flat surface 101 chamfered and rounded as with all other edges 102 of the C-arm detector cover device. FIG. 3 further reflects several additional features that enable this embodiment to fit snugly over a C-arm detector that is laterally connected to and protrudes horizontally from the C-arm of the imaging device. In this example, eyelets 303 are positioned on the bottom edges of the sidewall flanges 103 so that a zip tie or similar flexible compressive device may be threaded through all said eyelets 303 below the horizontal plane reflecting the bottom edge of the C-arm detector, and compressing said compressive device below that plane would pull the sidewall flanges 103 inward such that the entire device fits snugly over the C-arm detector. In other embodiments, such a compressive device may not be necessary where the overall shape of the design conforms sufficiently to the shape of the collector such that it remains in place without any circumferential pressure, where the inner surfaces of the sidewall flanges 103 contain dowel pins or other fastening devices enabling the apparatus to be snapped in position when placed on the detector, or where the inner surfaces of the sidewall flanges 103 and the underside of the flat surface 101 are covered with an adhesive to secure the apparatus to the detector or to a flexible cover draped over the detector. In this embodiment, two sidewall flanges are also positioned at an angle 304 to fit snugly along each angled lateral side of the neck connecting the C-arm detector to the C-arm, and leaving a gap 305 for the horizontally protruding C-arm. FIG. 3 also contains other elements that were introduced previously in connection with FIG. 1 and FIG. 2.

Figure 4:
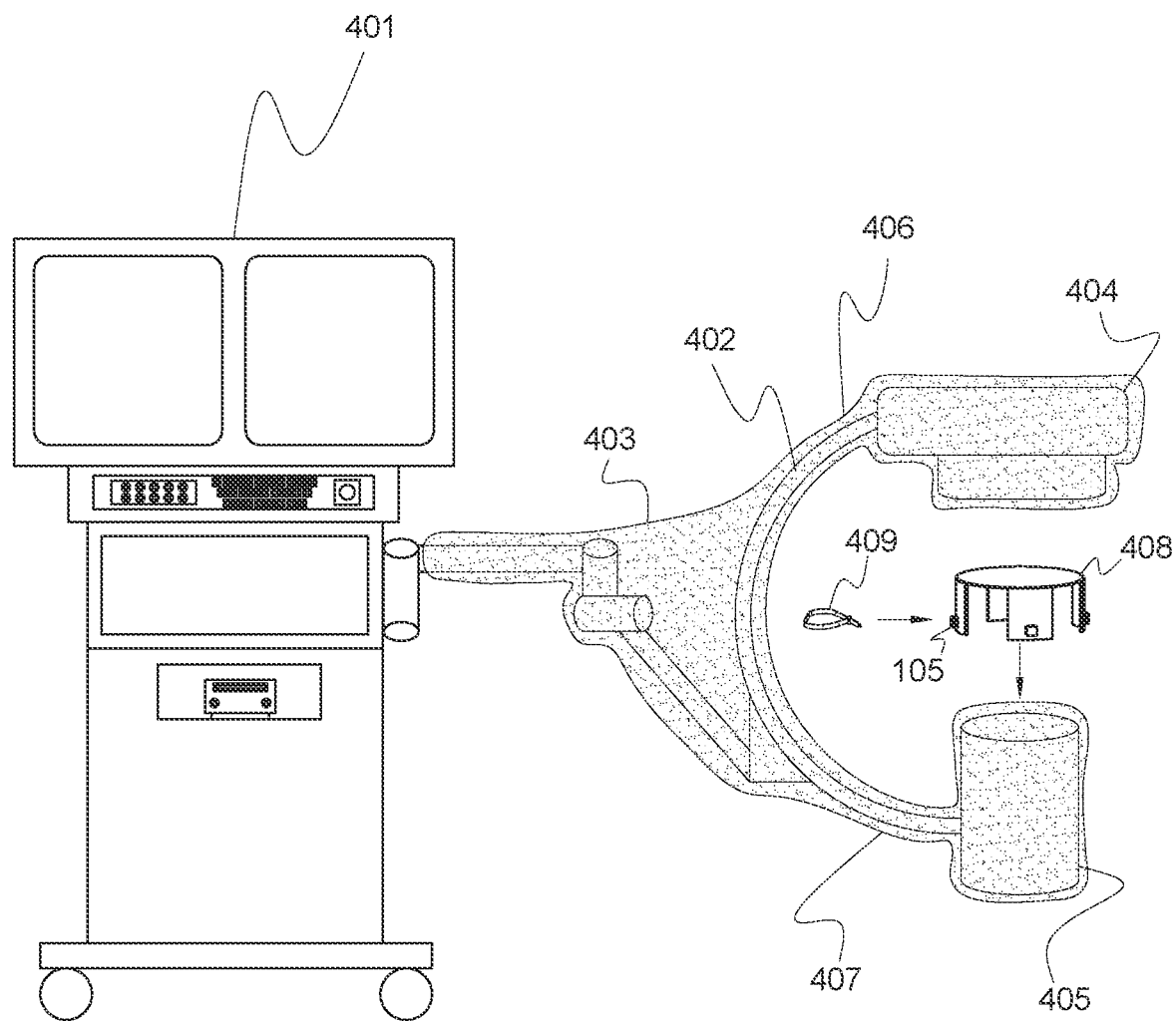
FIG. 4 is an elevation view of a C-arm intraoperative imaging device illustrating how the C-arm detector cover in FIG. 1 would be placed over the C-arm detector according to an embodiment of the present invention. This view also illustrates one method of securing the C-arm detector cover with a compressive device such as a "zip tie."
Figure 5:
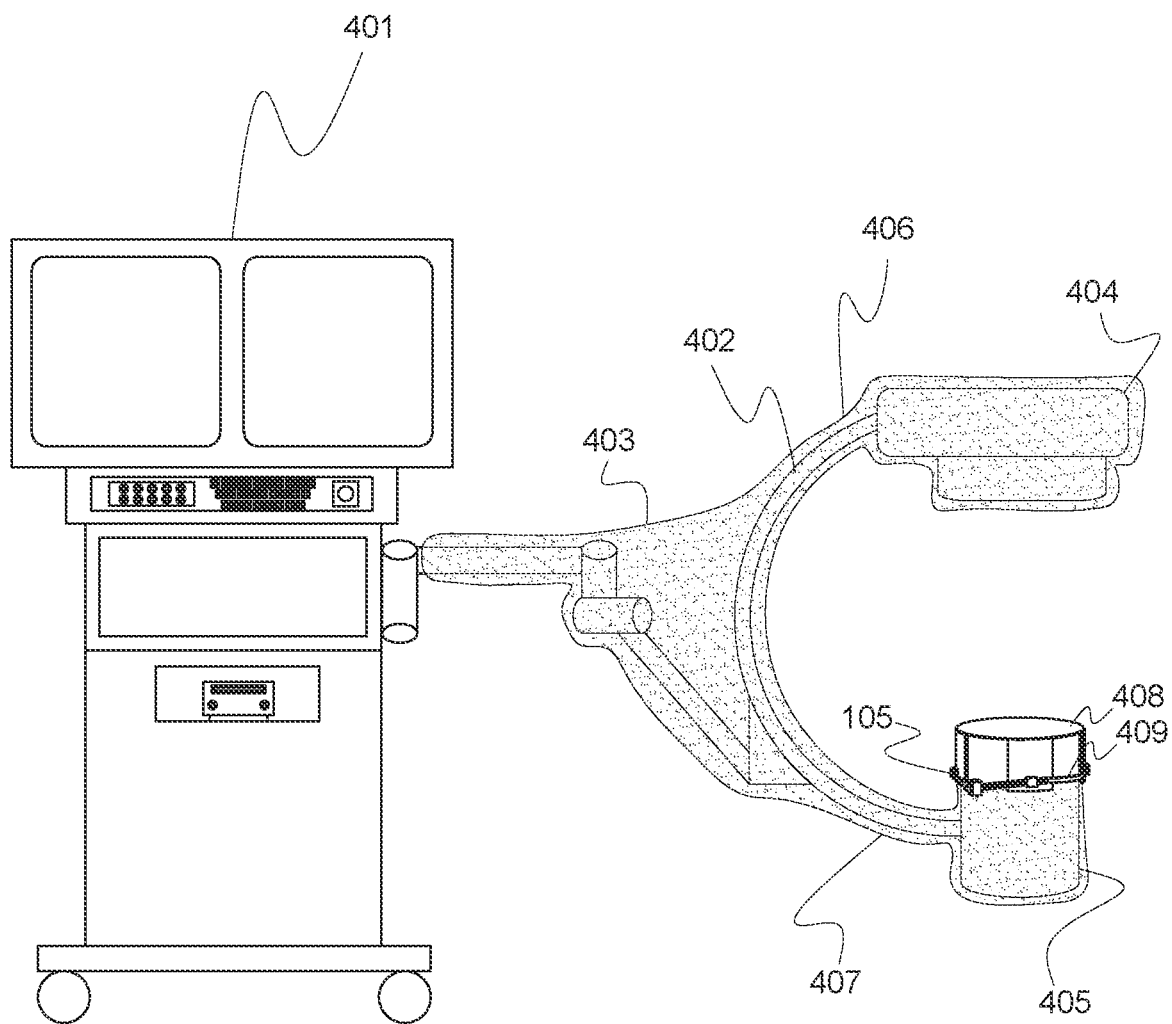
FIG. 5 is an elevation view of the C-arm intraoperative imaging device in FIG. 4 illustrating the C-arm detector cover in FIG. 1 placed over and affixed to the detector according to an embodiment of the present invention. This image shows the compressive device, in this example a "zip tie," in place and routed through eyelets.

FIG. 4 and FIG. 5 illustrate how the embodiment of the present invention reflected in FIG. 1 and FIG. 2 would be positioned on the imaging machine in the operating room. In this example, an intraoperative imaging machine 401 features a C-arm 402 extending outward and that is draped with a flexible cover 403 customized for the particular size and shape of the imaging machine. The C-arm 402 is connected to an X-ray source 404, which in this example is positioned over the operating surface, and a detector 405, which is positioned beneath the operating surface. Ordinarily, the flexible cover 403 is pulled snugly to the C-arm 402 at a position 406 near the X-ray source 404 and at a position 407 near the detector 405, such that the flexible cover 403 is pulled back and will not interfere with the operating area. In this example, the embodiment of the present invention reflected in FIG. 1 and FIG. 2 is placed over the flexible cover 403 that is already draped over the cylindrical detector 405. The C-arm detector cover is also sterile so it can provide an operating surface 408. In this example, a zip tie 409 is threaded through the eyelets 105 on the C-arm detector cover so as to tighten it around the detector 405.

Figure 6:
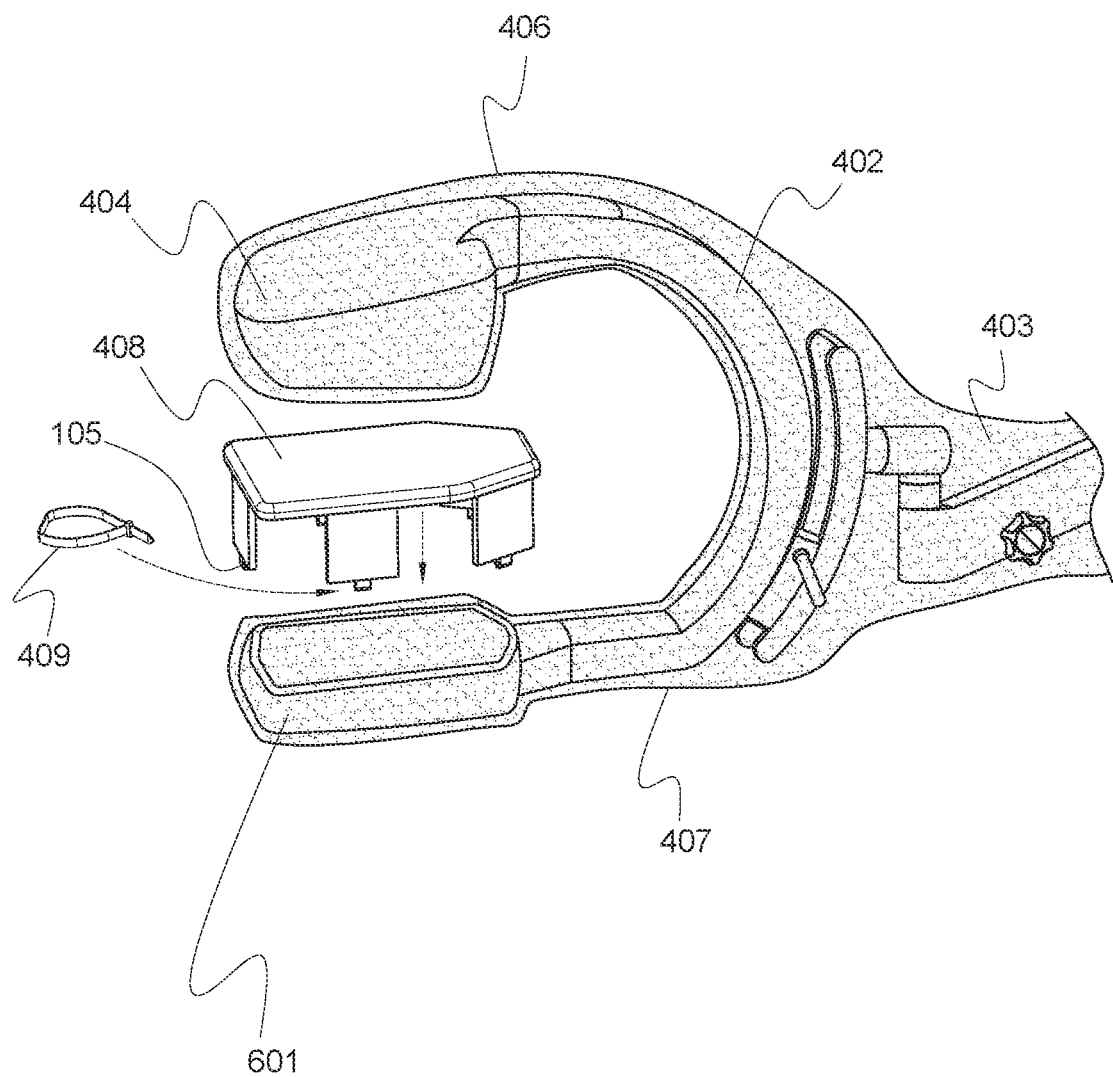
FIG. 6 is an elevation view of a C-arm intraoperative imaging device illustrating how the C-arm detector cover in FIG. 3 would be placed over the C-arm detector according to an embodiment of the present invention. This view also illustrates one method of securing the C-arm detector cover with a compressive device such as a "zip tie."
Figure 7:
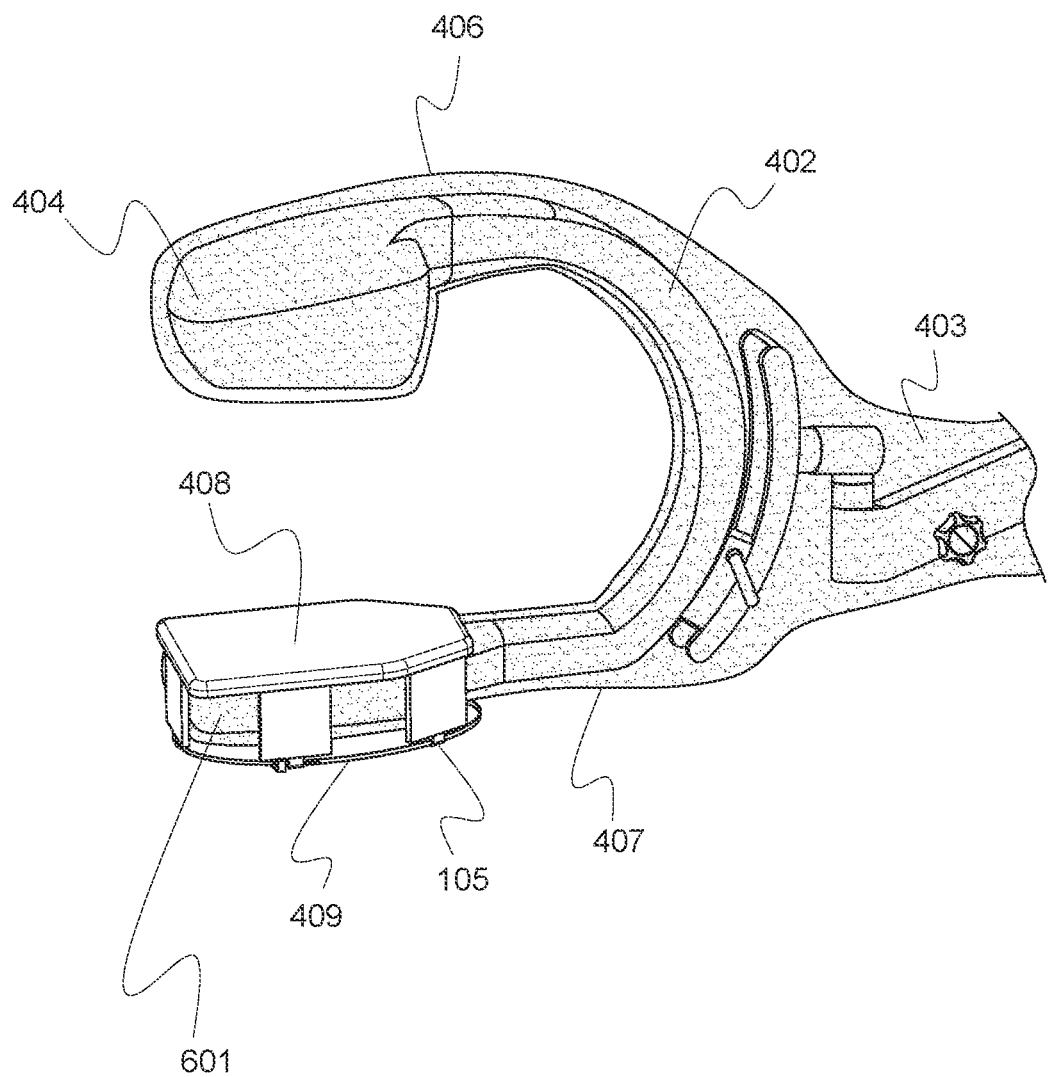
FIG. 7 is an elevation view of the C-arm intraoperative imaging device in FIG. 6 illustrating the C-arm detector cover in FIG. 3 placed over and affixed to the detector according to an embodiment of the present invention. This image shows the compressive device, in this example a "zip tie," in place and routed through eyelets.

FIG. 6 and FIG. 7 illustrate how the embodiment of the present invention reflected in FIG. 3 would be positioned on the imaging machine in the operating room. In this example, the C-arm 402 is positioned such that a detector 601 of oblong or rectangular shape is connected laterally to the horizontally protruding bottom edge of the C-arm. In this example, the embodiment of the present invention reflected in FIG. 3 is placed over the flexible cover 403 that is already draped over the oblong detector 601. In this example, a zip tie 409 is threaded through the eyelets 105 on the C-arm detector cover so as to tighten it below the plane of the bottom edge of the C-arm detector 601. FIG. 6 and FIG. 7 also contain other elements that were introduced previously in connection with FIG. 4 and FIG. 5.

It will be apparent to one skilled in the art that the C-arm detector cover provided in accordance with the present invention may be provided using some or all of the mentioned features or components without departing from the spirit and scope of the present invention. It will also be apparent to the skilled artisan that the embodiments described above are specific examples of a single broader invention which may have greater scope than any of the singular descriptions taught. There may be many alterations made in the descriptions without departing from the spirit and scope of the present invention.

What is claimed is:

1. A puncture-resistant radiolucent operating surface apparatus, comprising
   a flat radiolucent and puncture-resistant surface customized to cover and fit the shape and dimensions of a detector of a particular model of an intraoperative imaging machine; and
   downwardly extending sidewall flanges connected to said flat radiolucent and puncture-resistant surface and that are customized to snugly fit the shape and dimensions of the sides of said detector such that said sidewall flanges hold the entire apparatus stable when placed in position on said detector.

2. The puncture-resistant radiolucent operating surface apparatus of claim 1 wherein the entire apparatus is comprised of puncture-resistant material.

3. The puncture-resistant radiolucent operating surface apparatus of claim 1 wherein the sidewall flanges are positioned so as to leave a gap to accommodate a horizontally extending arm of a particular model of an intraoperative imaging machine.

4. The puncture-resistant radiolucent operating surface apparatus of claim 1 wherein the inner surfaces of the sidewall flanges contain dowel pins or other fastening devices enabling the apparatus to be snapped in position when placed on the detector.

5. The puncture-resistant radiolucent operating surface apparatus of claim 1 wherein its inner surfaces are covered with an adhesive to secure the apparatus to the detector or to a flexible cover draped over the detector.

6. The puncture-resistant radiolucent operating surface apparatus of claim 1 further including a mechanism to provide circumferential pressure around said sidewall flanges in order to stably secure the apparatus on the detector.

7. The puncture-resistant radiolucent operating surface apparatus of claim 6 wherein the mechanism for providing circumferential pressure consists of placing a zip tie, elastic, or other compressive band around the sidewall flanges of the apparatus.

8. The puncture-resistant radiolucent operating surface apparatus of claim 7 wherein the sidewall flanges of the apparatus contains eyelets through which to thread a zip tie, elastic, or other compressive band.

9. The puncture-resistant radiolucent operating surface apparatus of claim 6 wherein the mechanism for providing circumferential pressure is to connect the sidewall flanges to the flat surface at an acute inner angle such that the sidewall flanges apply lateral pressure around the sides of the detector.

10. A method of affixing a puncture-resistant radiolucent operating surface to a detector of a particular model of an intraoperative imaging machine, comprising
    covering said detector with a flat radiolucent and puncture-resistant surface customized to cover and fit the shape and dimensions of said detector, and
    securing said flat radiolucent and puncture-resistant surface to said detector with downwardly extending sidewall flanges connected to said flat radiolucent and puncture-resistant surface and that are customized to snugly fit the shape and dimensions of the sides of said detector to ensure that said flat radiolucent and puncture-resistant surface remains stable when placed in position on said detector.

11. The method of claim 10 further including providing circumferential pressure around the detector through the means of a zip tie, elastic, or other compressive band.

12. The method of claim 10 further including providing dowel pins or other fastening devices on the inner surfaces of the sidewall flanges of claim 10 so that said sidewall flanges can be snapped in position when placed on the detector.

13. The method of claim 10 further including providing circumferential pressure around the detector by affixing sidewall components to the flat surface at an acute inner angle such that the sidewalls apply lateral pressure around the sides of the detector.

14. The method of claim 10 further including affixing the operating surface onto the detector through the means of an adhesive.

* * * * *